United States Patent [19]

Langton

[11] Patent Number: 5,452,722
[45] Date of Patent: Sep. 26, 1995

[54] ULTRASOUND BONE ANALYSER

[75] Inventor: Christian M. Langton, Doncaster, Great Britain

[73] Assignee: McCue Ultrasonics, Ltd., Winchester, England

[21] Appl. No.: 80,920

[22] Filed: Jun. 22, 1993

[30] Foreign Application Priority Data

Jun. 22, 1992 [GB] United Kingdom ............... 9213220

[51] Int. Cl.⁶ .................................................. A61B 8/00
[52] U.S. Cl. ................... 128/660.06; 128/661.03
[58] Field of Search ................ 128/660.01, 660.02, 128/660.06, 661.03, 662.03

[56] References Cited

U.S. PATENT DOCUMENTS

| | | | |
|---|---|---|---|
| 3,847,141 | 11/1974 | Hoop | 128/774 |
| 4,237,901 | 12/1980 | Taenzer | 73/644 |
| 4,361,154 | 11/1982 | Pratt, Jr. | 128/660.01 |
| 4,476,873 | 10/1984 | Sorenson et al. | 128/660.01 |
| 4,774,959 | 10/1988 | Palmer et al. | 128/660.06 |
| 4,913,157 | 4/1990 | Pratt, Jr. et al. | 128/660.01 |
| 5,014,970 | 5/1991 | Osipov | 269/328 |
| 5,119,820 | 6/1992 | Rossman et al. | 128/661.03 |
| 5,134,999 | 8/1992 | Osipov | 128/661.03 |

FOREIGN PATENT DOCUMENTS

| | | |
|---|---|---|
| 299906 | 7/1988 | European Pat. Off. . |
| 341969 | 5/1989 | European Pat. Off. . |
| 2318240 | 6/1977 | France . |
| 2925933 | 3/1980 | Germany . |
| WO80/02796 | 6/1980 | WIPO . |
| WO90/01903 | 3/1990 | WIPO . |

OTHER PUBLICATIONS

A Contact Method for the Assessment of Ultrasonic Velocity and Broadband Attenuation in Cortical and Cancellous Bone (pp. 243 to 299, 1990 Institute of Physical Sciences in Medicine, vol. 11, No. 3, Printed in the UK.
Radiology, vol. 148, No. 3, Mar. 1981 pp. 701–710 Detroit, US M. A. Greenfield Measurement of Velocity of Ultrasound in Human Cortical Bone in Vivo–pp. 701–701 Medical & Biological Engineering & Computing, vol. 25, No. 6, Nov. 1987, pp. 620–626, Stevenage, Herts, GB. R. N. McCartney et al: "Combined 2.25 MHz ultrasound velocity and bone mineral density measurements in the equine metacarpus and their in vivo applications".

Primary Examiner—Francis Jaworski
Attorney, Agent, or Firm—Lackenbach Siegel Marzullo Aronson & Greenspan

[57] ABSTRACT

An ultrasound bone analysis apparatus having locating means (14) such as a foot bed, for locating a patient's body part in a predetermined position, and a pair of ultrasonic transducers (20, 22) for use in taking ultrasonic measurements of the body part. Each transducer includes a body part contacting portion (19), such as a silicone pad, for ultrasonic contact with the body part. The apparatus further includes means for moving the body part contacting portion of each transducer relative to the body part for allowing the contact of each transducer with the body part to be more accurately controlled. The apparatus also includes pressure control means for controlling the pressure with which the body part contacting portion of the transducers contacts the body part. This allows the compression of the body part contacting portion to be maintained at a constant value and therefore for the measurements to be more accurate.

16 Claims, 7 Drawing Sheets

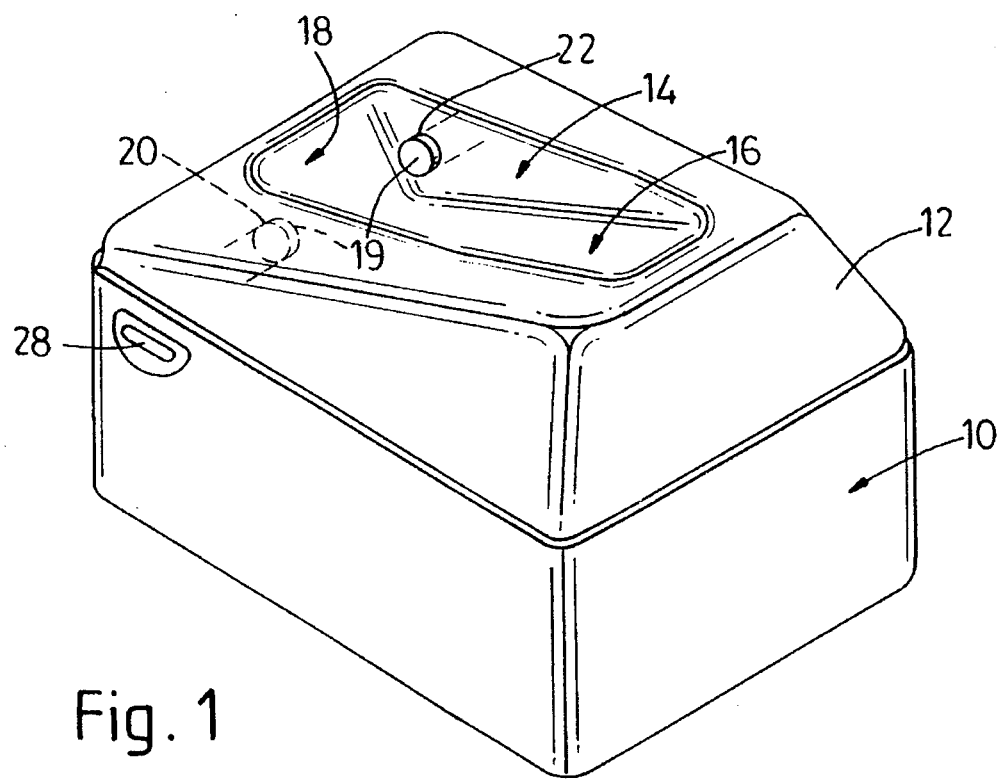
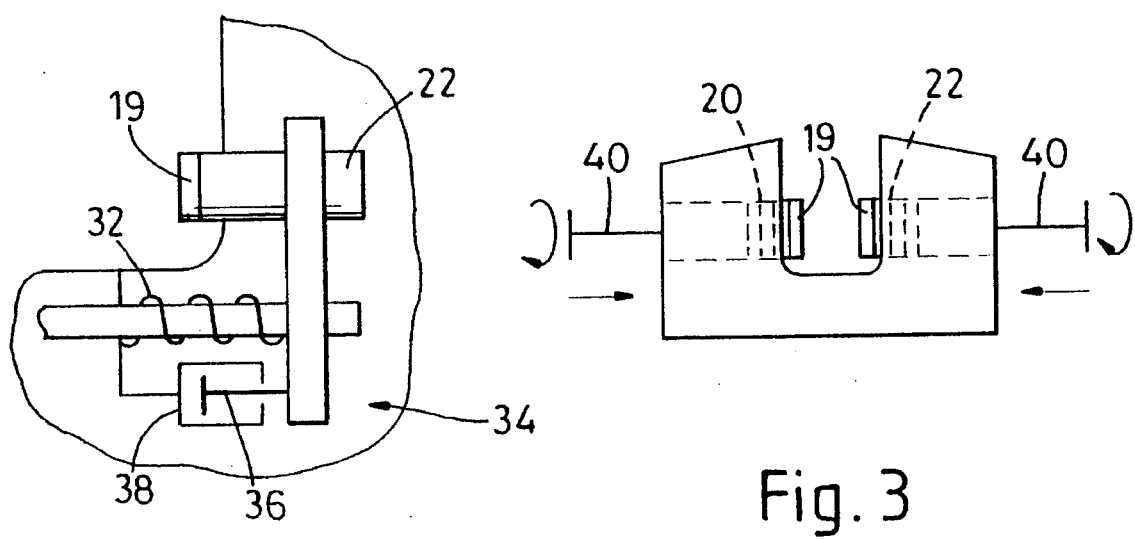
Fig. 1
Fig. 2
Fig. 3

ULTRASOUND BONE ANALYSER

FIELD OF THE INVENTION

The invention relates to an ultrasound bone analysis apparatus and in particular to such an apparatus for use in the field of human or veterinary medicine. It also relates to a method of use of an ultrasound bone analyser.

BACKGROUND ART

There is an increasing need for a simple and easily usable means whereby individuals most at risk from bone fracture due to osteoporosis, that is to say net loss of bone mineralisation, may be identified. Elderly persons are one of the groups most at risk of this condition and, as the average life expectancy increases, the incidence of bone fractures due to osteoporosis in the general population is increasing also.

Various devices are known for measuring bone density, including x-ray, gamma photon apparatus, and ultrasound apparatus. The latter are particularly advantageous in that they are basically non-invasive.

In the use of ultrasound, it has been known that the velocity of the signal through a patient's bone is a measure of the elasticity and density of the bone. However, it has more recently been found that by measuring broadband ultrasonic attenuation (BUA) there can be obtained data which is a measure of both the density and structure of cancellous bone. The data is expressed as the increase in ultrasonic attenuation with frequency in the range 200 kHz to 600 kHz.

One such device measures ultrasonic attenuation as ultrasound is transmitted through a bath of water, first without and then with a patient's foot immersed in the water. The data derived from the test is a measure of bone ultrasound attenuation.

A second such device, described in UK patent application GB 2257253 (published 6th Jan. 1993), includes a pair of ultrasonic transducers which, in use, contact the patient thus avoiding the need for a water bath. A silicone pad is attached to each transducer which, in use, contacts the patient's body part.

In the device of GB 2257253 one of the transducers is fixed and the other of the pair is movable. A patients body part e.g. heel, is placed against the fixed transducer and the movable transducer is then moved into contact with the body part. This allows the measurement to be taken.

One possible disadvantage with this apparatus is that the accuracy with which measurements can be repeated is limited. The pressure of the patient's body part against the fixed transducer may vary, the contact with that transducer (or indeed the other movable transducer) may also vary and the position of the patient's body part may change. Additionally, the pressure exerted by the movable transducer varies according to the size of body part i.e. according to the spacing between the transducers. Since the pressure exerted by the transducer affects the compression of a silicone pad on the transducer—and the ultrasound calculations made typically assume a constant compression in order to calculate the distance between the transducers— then this will affect the accuracy and repeatability of the measurements.

SUMMARY OF INVENTION

The present invention aims to alleviate some or all of the above problems.

Accordingly, in a first aspect, the present invention provides an ultrasound bone analysis apparatus having locating means (14) for locating a patients body part in a predetermined position, and a pair of ultrasonic transducers (20, 22) for use in taking ultrasonic measurements of said body part, each transducer including a body part contacting portion (19) for ultrasonic contact with the said body part, characterised in that the apparatus includes means for moving the body part contacting portion (19) of each transducer (20, 22) relative to said body part when said body part is located in the locating means.

In this way, by providing means for moving the body part contacting portions e.g. silicone pads, of both of the transducers more reliable ultrasonic contact can be achieved by both transducers with the body part.

The apparatus includes a pair of ultrasonic transducers, however this pair may be selectable from a number of different transducers e.g. to provide for transducers of different size, frequency or position to be selected.

In a preferred embodiment, the ultrasound bone analysis apparatus includes pressure control means for controlling the pressure with which the body part contacting portion of at least one of the transducers contacts the body part. If the pressure is controlled then the compression of the body part contacting portion may also be controlled and therefore the actual spacing between the pair of transducers may be more accurately known.

Preferably the body part contacting portion of the transducer is a silicone pad and the pressure control means is usable to ensure a predetermined compression of the pad upon contact with the body part. A typical predetermined compression may be e.g. 1 mm, and if the pressure control means is operated to ensure that this predetermined compression value is maintained regardless of the size of the body part (i.e. the spacing between the transducers) then that spacing may be more accurately known and more easily repeatable.

In a typical prior art system where, for example, the pair of transducers are biased towards each other e.g. by a spring, and are drawn apart to allow insertion of the body part between them, the pressure exerted by the spring will clearly be in proportion to its compression. This means that for larger body parts the pressure exerted is greater and therefore the body part contacting portions are more compressed and, if the calculations made assume a constant compression, the results may be inaccurate.

Preferably the apparatus includes adjustment means for adjusting the locating means to facilitate location of the body part relative to the transducers. In order to obtain accurate measurements it is important that the correct portion of the body part is adjacent the transducers. For example, when taking measurements of a human heel if the locating means are such that the correct portion of an adult heel will be adjacent the transducers, then when the apparatus is used on a child the heel may be incorrectly placed.

The locating means may comprise a shaped portion to accommodate the body part (e.g. foot bed for the above example) and the adjustment means may include at least one spacer means for adjusting a dimension of the shaped portion. In a practical embodiment the spacer means may include liners for insertion into the foot bed to reduce the available space in the foot bed. In the above example, this would have effect of raising the child's foot so that the correct portion of the heel was adjacent transducers. A number of different spacers may be provided to accommodate different sized body parts.

In a preferred embodiment the transducers may be removably mounted in mounting means, and the mounting means may then be attached to the means for moving the transducers. This would facilitate easier removal and interchangeability of the transducers.

It may be advantageous to use different size transducers on different sized body parts i.e. to obtain appropriate level of contact. For example, a transducer with a 19 mm diameter element may be appropriate for an adult heel whereas a transducer with a 12.5 mm diameter element may be more appropriate for a child's heel. Such different sizes of transducers may be then interchanged in the same bone analysis apparatus thus improving the scope of use of the apparatus.

Typically, the mounting means may be the UHF connector for the transducers and thus the UHF connector is connected to the moving means whilst leaving the transducer free to be removed and replaced.

The above examples cite the use of the apparatus with a human heel, but the apparatus may be equally suitable for use with other body parts or for veterinarian use such as with the leg bones of horses.

One possible use of the apparatus according to the present invention could be the monitoring of the development of certain diseases. In such uses it can be important to monitor small changes in bone size or structure and accordingly it is important that these changes are not overshadowed by any inherent statistical errors in the measurements made by the apparatus. To this end, as described above, the use of more accurate coupling mechanisms and accurate positioning on the heel can reduce such errors. Additionally, steps can be taken to improve the repeatability of the measurements through statistical means.

Accordingly, in a second aspect, the present invention provides a method of operating an ultrasonic bone analysis apparatus including the steps of:

(i) taking three successive measurements with the apparatus, (ii) determining if the three measurements fall within a predetermined range, and either:

(iii) if so taking the average of the measurements, or (iv) if not, taking a fourth measurement and determining if three of the four measurements fall within a predetermined range and either (v) if so, taking the average of the three measurements which fall within the predetermined range or, if not, repeating step (iv) as necessary.

The use of this method helps to reduce statistical errors in the measurements made and thus improve the accuracy of the equipment. Any number of measurements could be taken and the larger the number on measurements which are averaged the smaller will be the statistical deviation and possible error. Three measurements was selected as being the minimum number likely to result in suitable error level.

In a third aspect, the present invention provides a method of operating an ultrasound bone analysis apparatus, the apparatus having a pair of ultrasonic transducers (20, 22) for use in taking ultrasonic measurements of a patients body part, including the steps of:

(i) moving a body part contacting portion (19) of each transducer into ultrasonic contact with said body part, and (ii) controlling the pressure with which the body part contacting portions contact the body part.

As explained above, control of the pressure can reduce errors through reducing variations in compression of the body contacting portion. Preferably the above method further includes the step of adjusting the pressure to a predetermined value in order to ensure a predetermined compression of the body part contacting portion.

There are various possibilities for the structure of the apparatus. The moving means acting on at least one of the transducers for bringing the pair of transducers into contact with the patient's body part may include spring means and damping means for limiting the rate of movement of said at least one of the transducers under the action of said spring means. The damping means may be constituted by a piston movable in a volume of fluid.

Alternatively, the means for bringing the transducers into contact with the patient's body part may be hydraulic or pneumatic, or may be constituted by a motor driven mechanism for advancing or retracting at least one of the transducers and a pressure sensor arranged to switch the motor off at a predetermined contact pressure.

The analyser may include means for locating the at least one of the transducers in a position remote from the other to facilitate the positioning of the patient's body part between them, said means preferably being constituted by a locking mechanism requiring a rotational movement of a handle part to lock it or release it.

Means may also be provided whereby the transducers are movable with equal and opposite motion by the operation of a single handle, conveniently by means of a flexible wire and pulley arrangement for example. There may be a certain amount of lost motion provided between the two transducers in order to allow for unequal heel measurements i.e. if one transducer contacts the heel before the other, the other may continue to move so as to also conatct the heel. The arrangement will preferably be such that when in their open position, enabling the positioning of the patient's body part between them, the transducers are located wholly within portions of the mounting member which flank the location for the patient's body part.

Means will preferably be provided for automatically recording the separation distance between the pair of ultrasonic transducers. Such means may be constituted by a linear precision potentiometer including a variable resistor or by a linear variable differential transformer. In an arrangement in which the means for bringing the transducers into contact with the patient's body part are constituted by motor driven mechanism, the or each motor may be a stepping motor and by the recording of the number of steps of known translation may give the transducer separation automatically.

BRIEF DESCRIPTION OF DRAWINGS

Embodiments of the present invention will now be described with reference to the accompanying drawings in which FIG. 1 is a perspective view of an ultrasound bone analyser embodying the invention, FIG. 2 illustrates means for moving the transducers of an ultrasonic bone analyser, FIG. 3 illustrates means for locking the transducers in an open position.

DETAILED DESCRIPTION OF EMBODIMENTS

Figure 4:
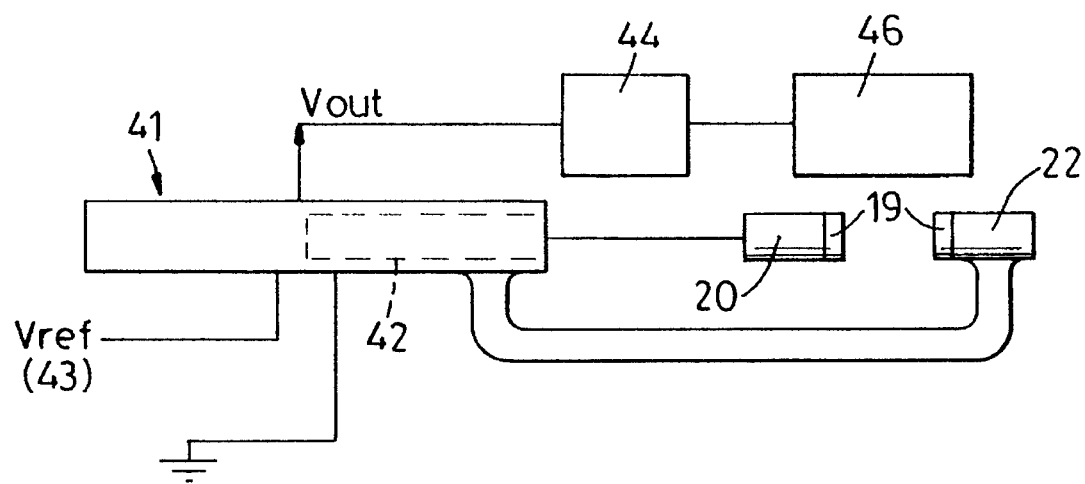
FIG. 4 illustrates a transducer separation distance measuring mechanism.

Referring now to Figure i of the drawings, an ultrasound bone analyser suitable for analysis of a human heel is there illustrated. The analyser includes a mounting member generally indicated 10 of box-like form with a top cover 12 which has been moulded with locating means such as a central depression 14. The depression 14 is of a suitable shape and size for receiving a patient's foot with the sole of the foot pressed against a surface 16 and with the back of the heel resting against a surface 18 at rather more than a right angle to the surface 16.

The device also includes a pair of in line on co-axial ultrasonic transducers 20 and 22 (one acting as a transmitter and one as a receiver) which project from side surfaces of the depression 14. The opposed faces of the two transducers are provided with respective body part contacting portions 19 such as silicone pads (see FIG. 6).

The arrangement is such that when a patient's foot is located in the depression 14, the pair of transducers 20 and 22 are positioned on the opposite sides of the patient's heel bone (Calcaneum) the characteristics of which are to be measured. The transducers are both slidably mounted towards and away from each other, and when a patient's foot has been located in the depression 14, said pair of transducers can be brought into contact with the opposite sides of the patient's heel.

Alternatively, for example, the mounting member may be differently shaped for receiving a different patient body part (or for receiving a horse's leg for example). A number of different ultrasonic transducers may be provided for use in the analyser in the range of ½ MHz to 10 MHz. Also a number of transducers may be provided for taking different measurements, or measurements in different directions.

Referring now to FIG. 2, means are provided for bringing the silicone pads 19 of the pair of ultrasonic transducers 20 and 22 into contact with the patient's heel. These means may include respective tension springs 32 and damping means generally indicated 34. The damping means 34 are shown to be constituted by a piston 36 fixed in effect to the transducer and movable in a volume of fluid in a cylinder 38 fixed with respect to the mounting member 10.

In the operation of the device, when a patient's foot has been located in the device, a locking mechanism holding the transducers widely apart can be released so that said transducers move towards the patient's heel under the force of the springs 32, the movement being damped by the dampers 34. The silicone pads of the transducers are thus brought to bear gently against the patient's heel and preferably contact the heel with high repeatability, that is to say will bear against the heels of different patients with substantially the same pressure.

This is important for helping to ensure consistent results when using the analyser to test the bone condition of different patients, or indeed for testing the bone condition of a single patient at regular time intervals to determine whether there is any measurable change taking place.

Referring now to FIG. 3, the locking mechanism referred to for holding the transducers widely apart may be such as to require e.g. a quarter turn rotary movement of respective handles 40 to release them. As shown by the chain-dotted lines in FIG. 10, when in their open position, that is to say when spaced widely apart to facilitate the positioning of the patient's heel between them, the transducers may be located wholly within portions of the mounting member which flank the location for the patient's foot. They can thus be protected from damage.

FIG. 4 illustrates the provision of means for measuring, and possibly automatically recording, the separation distance between the pair of ultrasonic transducers. Such means may be constituted by a linear precision potentiometer 41 including a variable resistor 42 arranged to be varied in direct response to the spacing of the two transducers. In order to convert the resistance measurement to a distance measurement, an analogue to digital converter 44 and a computer 46 may also be included.

The separation distance between the pair of ultrasonic transducers is required for calculating the thickness of a bone the condition of which is to be tested. The distance between the pair of transducers when they have been brought into contact with a patient's body member, less the thickness of muscle and subcutaneous fat, is the thickness of bone at that point.

In FIG. 4, Vref indicates reference D.C. voltage source 43 and Vout is the output voltage of the variable resistor 41. Vout depends on the resistance ratio of the variable resistor, which in turn depends on the separation of the transducers. If R1 is the resistance between the Vout terminal and ground, and R2 the resistance between the Vout terminal and the Vref terminal, the Vout is given by the equation:

$$Vout = \frac{Vref R1}{R1 + R2}.$$

Alternatively, instead of the means illustrated in FIG. 4, there could be employed a linear variable differential transformer, or any other form of distance measurement.

Figure 5:
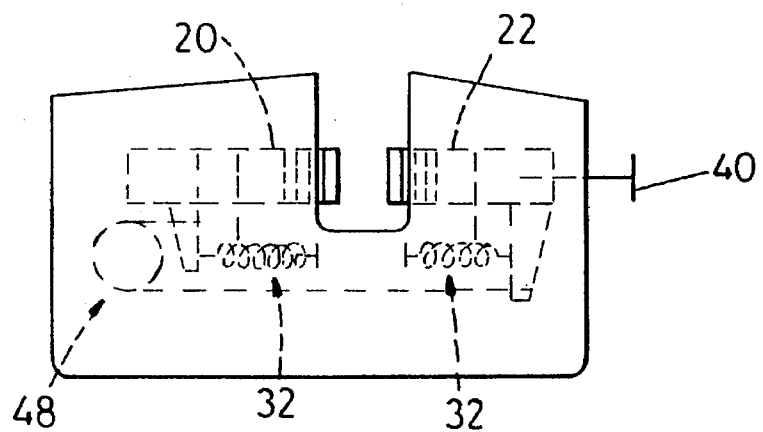
FIG. 5 illustrates a further transducer moving system.

Various modifications may be made. For example, in FIG. 5 there is illustrated an arrangement in which a handle 40 is connected to only one of the ultrasonic transducers. A flexible wire and pulley arrangement 48 is provided to connect the two transducers whereby they are movable with equal and opposite motion by the operation of the single handle against the force of respective tension springs 32,32. There may be a certain amount of lost motion provided between the two transducers in order to allow for unequal heel measurements i.e. if one transducer contacts the heel before the other, the other may continue to move so as to also conatct the heel.

Figure 6:
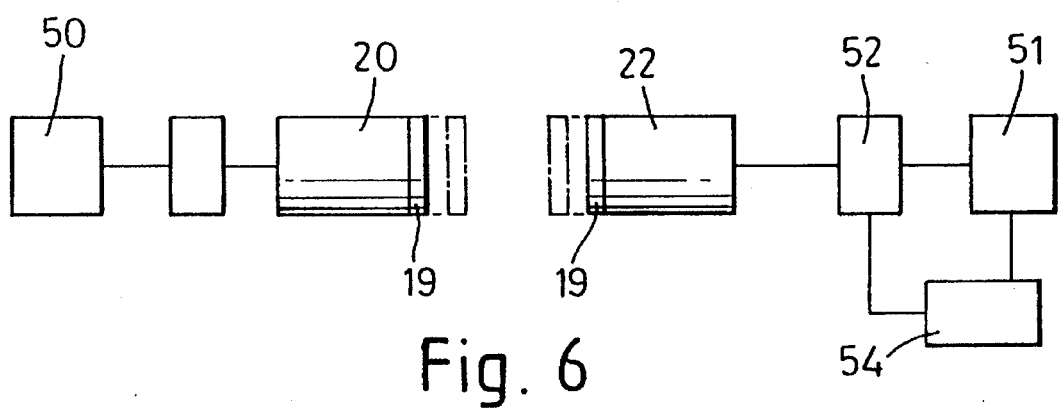
FIG. 6 illustrates a motor driven mechanism for moving the transducers.

In FIG. 6 there is illustrated a further possible modification in which the means for bringing the silicone pads of the ultrasonic transducers into contact with the patient's heel are constituted by motor driven mechanism for advancing or retracting the transducers, this mechanism including respective electric motors 50,51 and a pressure responsive sensor 52 for switching the motors on and off by way of a controller 54.

The pressure responsive sensor may monitor the pressure of the transducers against the patient's heel and in that way a consistent pressure of the silicone pads against a patient's heel can be achieved. It may be advantageous if the motors 50,51 are stepping motors because by the recording of the number of steps of known translation there can automatically be obtained a direct reading of the transducer separation. Alternatively, the means for moving the transducers and/or the pressure sensor may be hydraulic or pneumatic.

Figure 7:
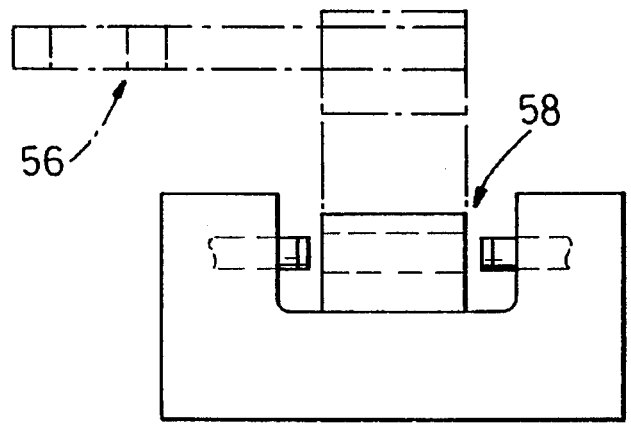
FIGS. 7 & 8 illustrate the calibration of a bone analyser.
Figure 8:
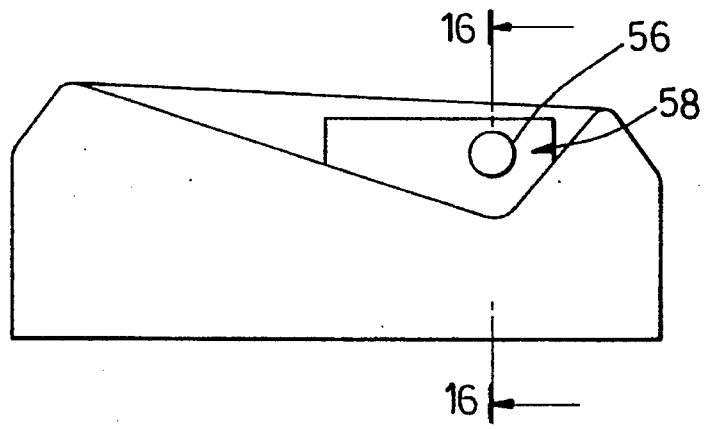
Figure 17:
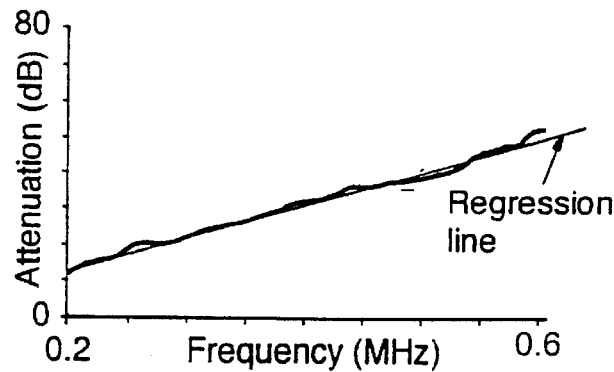
Figure 18:
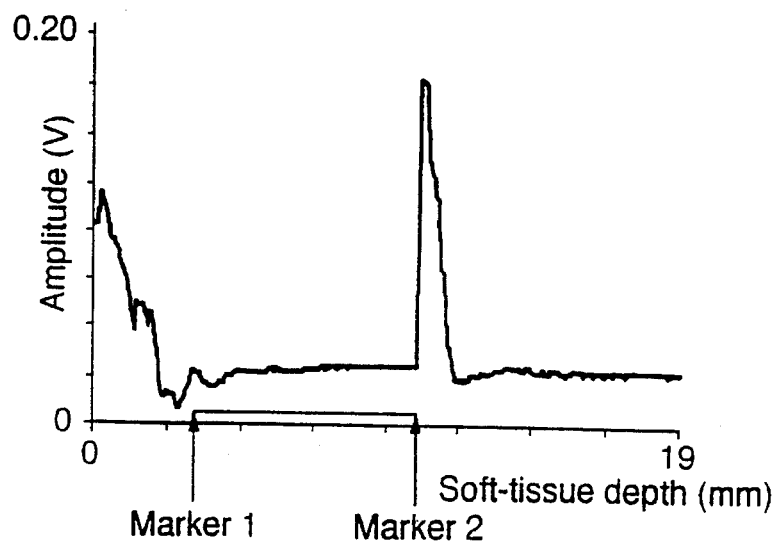

In FIGS. 7 and 8 there is illustrated the use of a calibration method for an ultrasound bone analyser of the kind described above, the method including the use of a container 56 for a quantity of a "phantom" material mimicking cancellous bone. The container can be located in a holder 58 placed in position in the locating means for a patient's body part so that the container is located between the ultrasonic transducers. The container in FIG. 17 is shown to have three separate compartments, the endmost compartments being filled with de-gassed water and the center compartment being filled with the material mimicking cancellous bone, for example a porous plastics material or a porous metal.

It is proposed to provide a set of different "phantom" material containers 56 and a reference container for selective use, these preferably being color coded. The "Phantom" containers may be arranged to give a read-out mimicking bone without loss of mineralization, bone with some average loss of mineralization, and bone with severe loss of mineralization. The containers 56 may all be of the same overall length, with the de-gassed water in the endmost compartments acting as acoustic spacers.

Figure 9:
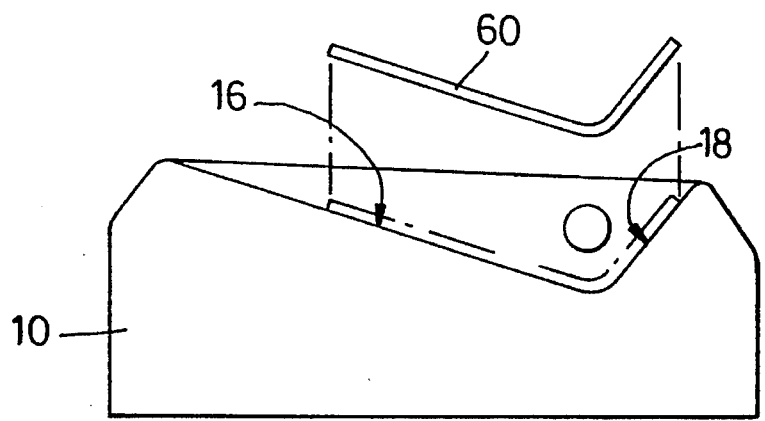
FIG. 9 illustrates spacer inserts for the bone analyser of FIG. 1.

In FIG. 9 there is illustrated the provision of spacer means 60, which can be used in association with the locating means for the patient's body part, having regard to the size of said body part. In other words, if the patient is a small child, the spacer means 60 can be placed in the depression 14 of the mounting member 10 to ensure that the patient's heel bone (Calcaneum) will be positioned between the pair of transducers. There may be provided a plurality of such spacer means of different thickness for selective use according to the size of the patient.

The operation of one embodiment of a bone analyser according to the present invention will now be described with reference to FIGS. 10 to 18.

Figure 10:
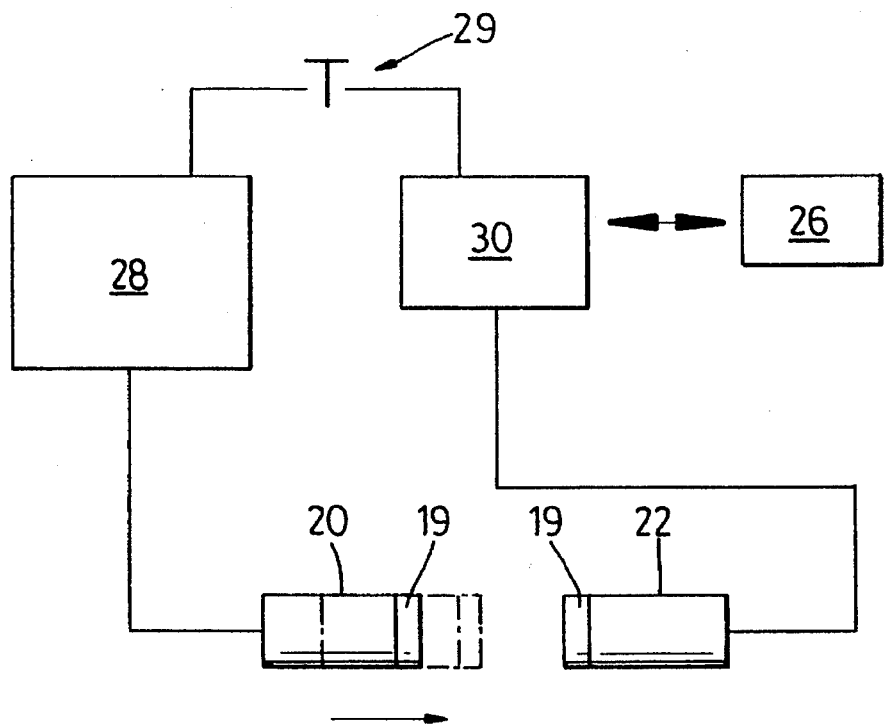
FIG. 10 is a block diagram of electronic apparatus forming part of the analyser

FIG. 10 shows a schematic representation of the electronic apparatus for one embodiment of a bone analyser. A computer 26 such as an IBM PC-compatible portable computer, is interfaced to a combined spike generator (transmitter) 28 and digital receiver 30 with dedicated menu-driven software. A trigger 29 is provided to initiate an ultrasonic pulse. The transducers 20 and 22 may be 1 MHz transducers e.g. of, 19 or 12.5 mm diameter. This apparatus may be used for velocity/BUA measurement.

Figure 11:
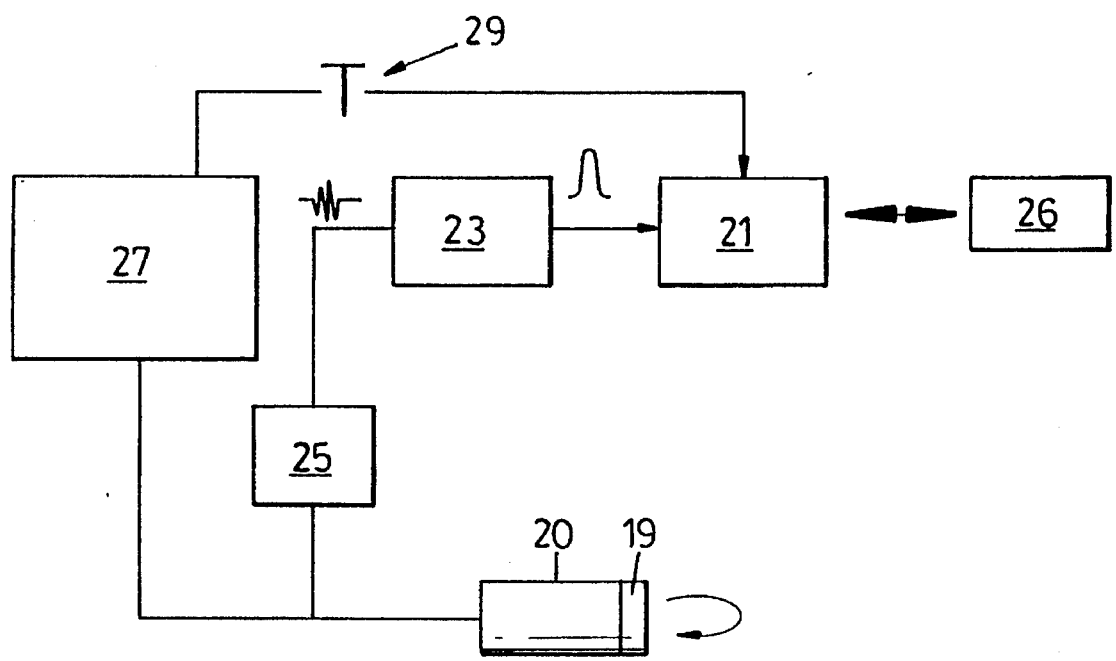
FIG. 11 is a block diagram of a second set of electronic apparatus.

An alternative set up, for use on soft tissue measurement, is shown in FIG. 11. Soft-tissue thickness is measured using, for example, a high resolution 5 MHz transducer, in pulse-echo mode, linked to a spike generator 27 and digital receiver 21, and the data displayed in the form of an A-scan (see FIG. 18). In FIG. 11, a portable computer 26 is shown to be interfaced to a spike generator and receiver, the receiver apparatus including a clipping circuit 25, a rectifying and smoothing circuit 23 and digital receiver 21. (The ultrasonic transducer 20 shown in FIG. 11 for the measurement of soft tissue may or may not be a different transducer from that shown in other views).

Figure 12:
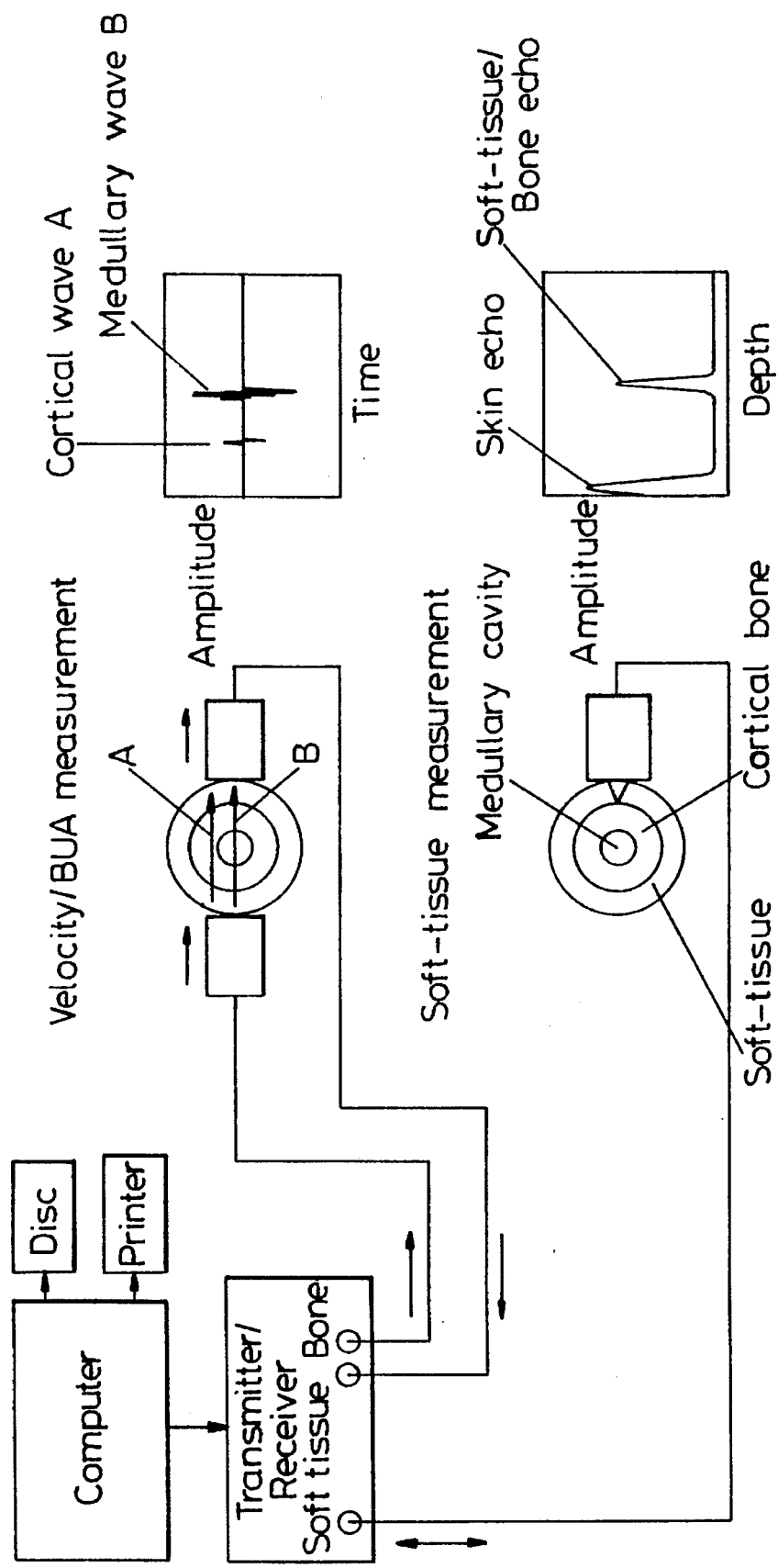
FIG. 12 is a block diagram of a third set of electronic apparatus.

Alternatively the two configurations of FIGS. 10 and 11 may be combined into one apparatus, as shown in FIG. 12.

FIG. 12 shows a block diagram of a CUBA (contact ultrasonic bone analyser) system. For velocity and BUA measurements the two transducers are placed around the bone, one acting as transmitter, the other receiver. In the case of a mid-diaphysis cortical bone measurement, two ultrasonic signals are detected, corresponding to transmission through the outer cortical shell (A) and through the central medullary cavity (B) respectively. In the case of a metaphyseal cancellous bone measurement, a single ultrasonic signal is detected. For soft-tissue measurement, a single transducer in pulse-echo mode is placed against both sides of the bone. For each measurement an A-scan is produced from which the depth of subsutaneous fat and muscle/ligament may be determined.

During operation, a screen of the computer (see FIG. 13) initially displays a transmission ultrasonic signal. The amplitude and time sensitivity may be controlled via a keyboard. For the calculation of velocity, the transit time is obtained via a digital timebase expansion method, see FIGS. 13 and 14, or alternatively may be automated in the software associated with the equipment. The software may detect the leading edge of the received ultrasonic signal.

Figures 13, 14:
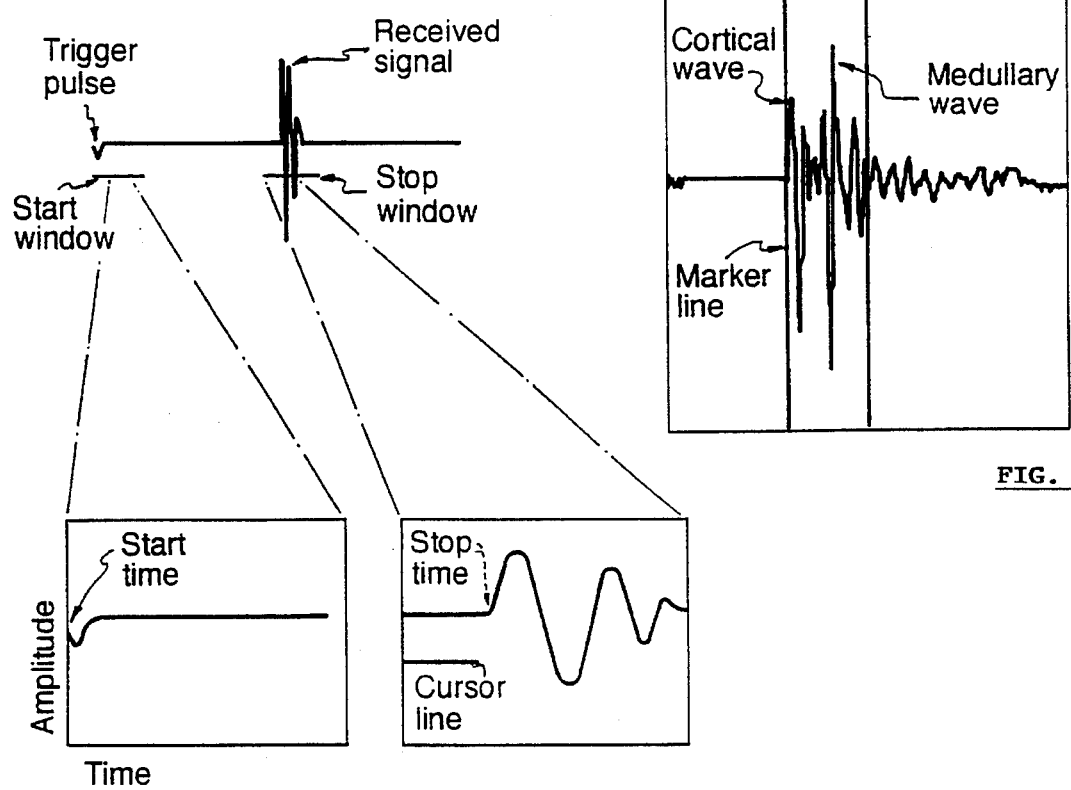
FIGS. 13 to 18 illustrate features of the operation of the apparatus.
Figure 15:
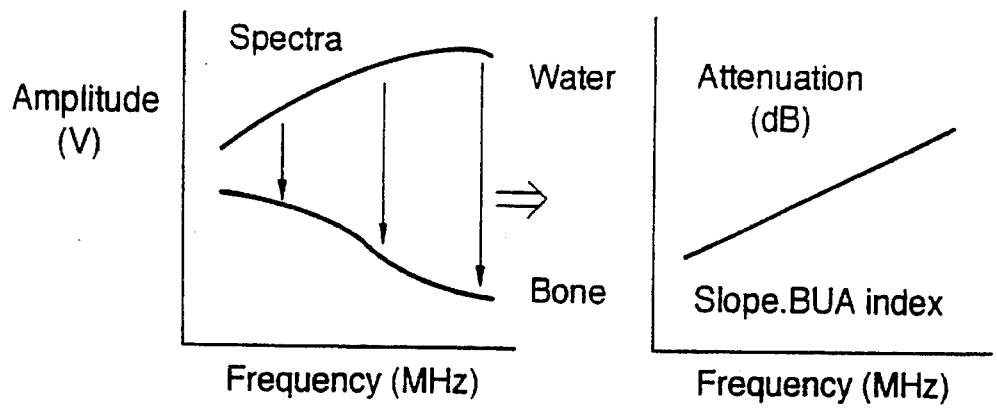

FIG. 13 is a representation of an initial screen where 4096 collected data points of the ultrasound signal are displayed on 256 horizontal screen pixels. By expanding a small region (window) of the screen, the 256 data points of that window may be displayed on the 256 horizontal screen pixels. As shown in FIG. 13, the user defines two windows, one containing the beginning of the required transit time measurement, and a second containing the end of the transit time. Normally, the beginning of the transit time corresponds to the transmission of the ultrasonic pulse, that is, the initial data point when the trigger 29 is actuated.

Once a time window has been selected, the user positions a screen marker via the keyboard as the beginning° of the detected ultrasonic pulse of interest, as shown in FIG. 4. Transit time is measured from the beginning of the first window (trigger pulse) to the arrival of the chosen ultrasonic signal in a subsequent window. The transit time and corresponding velocity calculation may then be displayed. The precision of velocity measurement is typically 0.2% (based on 4 cm bone sample at 2500 $ms^{-1}$ measured at 5 us per division), since the resolution of time measurement is 1% of the timebase sensitivity and the resolution of transducer separation is 0.01 mm. The resolution may be improved by using a faster digitisation rate.

Attenuation data is calculated by subtracting the amplitude spectrum for a test sample from one obtained for a reference material, for example de-gassed water (see FIG. 7). Comparison of the amplitude spectra provides the relationship between attenuation and ultrasonic frequency and measurement of the cortical and cancellous bone may be made.

A fast Fourier transform (FFT) algorithm is used to calculate the amplitude spectrum for a selected portion of the received signal. The FFT window may be selected via the software for the transit time. The resulting amplitude spectrum for the reference sample may be stored on disc for subsequent comparison with the spectrum for the test sample.

Figure 16:
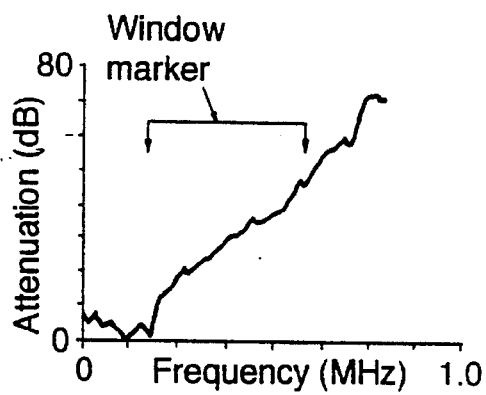

FIG. 16 shows a screen display of a typical attenuation trace. The software stores both the time domain (received signal) and frequency domain (amplitude spectrum) for the test sample on disc thus enabling additional data analysis if required.

In the attenuation trace shown in FIG. 16, the position and width of a selected frequency window is shown to be indicated by a window marker, this being controlled via the keyboard. The start and stop frequencies are indicated and enable an additional spot frequency attenuation facility. The selected frequency window (typically 200 kHz to 600 kHz) is shown in FIG. 17 to have been re-plotted with regression analysis to provide an index of BUA.

As mentioned earlier, when soft tissue is being measured the data may be displayed in the form of an A-scan. The depth range of the A-scan display may be varied, the indicated value of 19 m.m. being based on an average soft-tissue velocity of 1540 m s$^{-1}$. Tissue thickness d is calculated using d=v.t where v is a user defined tissue velocity and t is the measured transit time. Screen cursors enable two independent compartment measurements to be performed (see FIG. 18). The user defines the two velocities, in most cases these being chosen to represent subcutaneous fat (1450 m s$^{-1}$) and muscle (1580 m s$^{-1}$) respectively.

For small soft-tissue thicknesses, a stand-off may be incorporated in which case the first marker is positioned over the echo corresponding to the stand-off, and the second marker positioned over the soft-tissue echo of interest. Soft-tissue thickness may be recorded for both medial and lateral sides. Thus, the transducer separation and transit time may be corrected to allow a velocity to be measured in bone alone. Consequently, for soft-tissue correction of velocity, so-called limb velocity is obtained by dividing the transducer separation by the total transit time, the overlying soft-tissue thickness is subtracted from the transducer separation, and the corresponding soft-tissue transit time is subtracted from the total transit time. The true bone velocity is obtained by dividing the thickness of the bone by the transit time through it.

The corrected bone thickness may be incorporate into the BUA index, presented as dB MHz–$^1$ cm- a volumetric parameter. The transit time of the silicone pads 19,19 may be automatically normalised within the system algorithm.

I claim:

1. An ultrasound bone analysis apparatus having: locating means (14) for locating a patient's body part in a predetermined position, a pair of co-axial ultrasonic transducers (20, 22) for use in taking ultrasonic measurements of said body part, each transducer including a body part contacting portion (19) for ultrasonic contact with said body part, and one of said transducers acting as a transmitter and the other as a receiver; and means for moving the body part contacting portion (19) of each transducer (20, 22) relative to said body part when said body part is located in the locating means, whereby said means permit said measurements to be taken at a plurality of transducer separation distances to facilitate accommodation of differently sized body parts.

2. An ultrasonic bone analysis apparatus according to claim 1 including pressure control means for controlling the pressure with which the body part contacting portion of at least one of the transducers contacts said body part.

3. An ultrasonic bone analysis apparatus according to claim 2 wherein the body part contacting portion of the transducer is a silicone pad and the pressure control means ensures a predetermined compression of the pad upon contact with said body part.

4. An ultrasonic bone analysis apparatus according to claim 3 wherein the predetermined compression of the pad is substantially constant irrespective of the dimensions of said body part.

5. An ultrasonic bone analysis apparatus according to claim 1 including adjustment means for adjusting the locating means to facilitate location of said body part relative to the transducers.

6. An ultrasonic bone analysis apparatus according to claim 5 wherein the locating means comprises a footbed and the adjustment means includes at least one spacer means for adjusting a dimension of the footbed.

7. A ultrasonic bone analysis apparatus according to claim 1 in which the transducers are removably mounted in mounting means, the mounting means being attached to the means for moving the transducers.

8. An ultrasound bone analyser apparatus according to claim 1, including means for recording the measuring distance between said transducers.

9. An ultrasound bone analyser apparatus according to claim 1, wherein bone thickness is measured of a patient's heel bone (calcaneum).

10. An ultrasound bone analyser apparatus according to claim 1, wherein said transducers are operable in the range of ½ MH$_z$ to 10 MH$_z$.

11. A method of operating an ultrasonic bone analysis apparatus, the apparatus having a pair of co-axial ultrasonic transducers (20, 22) for use in taking ultrasonic measurements of a patient's body part, including the steps of:

(i) moving a body part contacting portion (19) of each transducer into ultrasonic contact with said body part, (ii) controlling the pressure with which the body part contacting portions contact the body part, and (iii) adjusting said pressure to a predetermined value to ensure a predetermined compression of the body part contacting portion.

12. A method of operating an ultrasonic bone analysis apparatus having a pair of co-axial ultrasonic transducers (20, 22) for use in taking ultrasonic measurements of a patient's body part in accordance with claim 1, including the steps of:

(i) taking at least three successive measurements with the apparatus (ii) determining if the at least three measurements fall within a predetermined range, and either:

(iii) if so taking the average of the measurements, or (iv) if not, taking a further measurement and determining if the at least three of the total measurements taken fall within a predetermined range and either, (v) if so, taking the average of the at least three measurements which fall in the predetermined range or, if not, repeating step (iv) as necessary; whereby statistical error in the measurements are reduced thereby improving the accuracy of said apparatus.

13. A method according to claim 12, wherein said patient's body part is removed from said apparatus and replaced between each measurement.

14. A method according to claim 12, wherein any number of measurements is taken.

15. A method according to claim 14, wherein the number of measurements taken are three.

16. An ultrasound bone analysis apparatus having locating means (14) for locating a patient's body part in a predetermined position, a pair of ultrasonic transducers (20, 22) for use in taking ultrasonic measurements of said body part, each transducer including a body part contacting portion (19) for ultrasonic contact with said body part, means for moving the body part contacting portion (19) of each transducer (20, 22) relative to said body part when said body part is located in the locating means, and pressure control means for controlling the pressure with which the body part contacting portion of at least one of the transducers contacts said body part, wherein the body part contacting portion of the transducer is a silicone pad and the pressure control means ensures that a predetermined compression of the pad is made upon contact with said body part, and the predetermined compression of the pad is substantially constant irrespective of the dimensions of said body part.

\* \* \* \* \*